US00PP10476P

United States Patent [19]

Koppe

[11] Patent Number: Plant 10,476

[45] Date of Patent: Jun. 30, 1998

[54] BEGONIA PLANT NAMED 'BELLONA'

[75] Inventor: Lubbertus H. Koppe, Ermelo, Netherlands

[73] Assignee: M. Koppe B.V., Ermelo, Netherlands

[21] Appl. No.: 673,827

[22] Filed: Jun. 27, 1996

[51] Int. Cl.[6] ..... A01H 5/00

[52] U.S. Cl. ..... Plt./87.18

[58] Field of Search ..... Plt./87.18

[56] References Cited

U.S. PATENT DOCUMENTS

P.P. 9,523 4/1996 Koppe ..... Plt./87.18

OTHER PUBLICATIONS

UPOVROM Disk 1997/01 Name Search Printout (1), 1997.

UPOVROM Disk 1997/01 Name Search Printout (2), 1997.

*Primary Examiner*—Howard J. Locker
*Assistant Examiner*—Kent L. Bell
*Attorney, Agent, or Firm*—Foley & Lardner

[57] ABSTRACT

A Begonia plant named 'Bellona' particularly characterized by flowering throughout the year, double-flowering with many rows of petals, bright and rich orange-red flower color, very good branching habit, strong and thick stalks, compact habit, dark foliage and outstanding keeping quality through the winter.

4 Drawing Sheets

The present invention relates to a new and distinctive cultivar of begonia plant, botanically known as *Begonia hiemalis* Fotch, and known by the cultivar name 'Bellona'.

The new cultivar is a random mutation of the begonia variety 'Barkos', disclosed in U.S. Plant Pat. No. 9,523, and was discovered by Lubbertus H. Koppe in July 1991 in Ermelo, The Netherlands.

The new cultivar was asexually propagated by the inventor for the first time in July 1992 in Ermelo, The Netherlands. Asexual reproduction by leaf cuttings has stably reproduced the unique features of the new cultivar through successive propagations.

The following characteristics distinguish the new begonia from its parent and other begonias commercially known and used in the floriculture industry:

1. 'Bellona' flowers throughout the year whereas many other begonias only flower during periods of long day-length.
2. 'Bellona' has a better branching than 'Barkos'.
3. Compared to 'Barkos', 'Bellona' produces more flowers.
4. The flowers of 'Bellona' are smaller than those of 'Barkos'.
5. The leaves of 'Bellona' are not as broad as those of 'Barkos'.
6. The plants of 'Bellona' are taller than those of 'Barkos'.
7. The flower color of 'Bellona' is orange-red whereas the flower color of 'Barkos' is red.
8. The keeping quality of 'Bellona' is outstanding.
9. 'Bellona' is strongly double-flowering with many rows of petals.

Of the many commercial cultivars known to the present inventors, the most similar in comparison to 'Bellona' is 'Betulia', which is described in copending application Ser. No. 08/673,826 filed Jun. 27, 1996. Chart A compares certain characteristics of 'Bellona' to those same characteristics of 'Betulia'.

CHART A

| Characteristic | 'Bellona' | 'Betulia' |
|---|---|---|
| Flower type | Double | Semi-double to double |
| Flower number | 7–9 from one stem out of axillary bud | 12–15 from one stem out of axillary bud |

CHART A-continued

| Characteristic | 'Bellona' | 'Betulia' |
|---|---|---|
| Plant size | 28–32 cm (height) × 33–36 cm (width) | 25–28 cm (height) × 30–34 cm (width) |
| Petal number | About 20 per flower | About 10 per flower |
| Foliage size | Larger than 'Betulia' | Smaller than 'Bellona' |

In general comparison to 'Betulia', 'Bellona' is larger and produces flowers that are double, larger, and greater in number.

The accompanying color photographs were taken on Oct. 8, 1995 in 's-Gravenzande, The Netherlands. Photographs were taken of 4 month old plants grown in 17 cm pots.

Sheet 1 is a side perspective of 'Bellona'.

Sheet 2 is the upper side of a mature leaf from the new cultivar.

Sheet 3 is a close-up of flowers from the new variety.

Sheet 4 is a side view of an inflorescence from 'Bellona'.

The new cultivar 'Bellona' is principally distinguishable from other begonia varieties by its orange-red double-type flowers and outstanding keeping quality. Asexual reproduction of the new cultivar has demonstrated that the combination of characteristics herein disclosed for the new cultivar are firmly fixed and stable through successive generations. 'Bellona' has not been observed under all possible environmental conditions. The phenotype may vary with variations in environment such as temperature, light intensity and day length, without a change in genotype.

The following is a detailed description of the new begonia cultivar based on plants produced under commercial practices in Maasland, The Netherlands. The observations were made of 4 month old plants grown in 17 cm pots.

Color references are made to The Royal Horticulture Society (R.H.S.) Colour Chart except where general terms of ordinary dictionary significance are used.

Classification: *Begonia hiemalis* Foch cv. 'Bellona'.

Propagation:

*Type cutting.*—Top and/or leaf cutting.

*Time to root.*—5 weeks at 20°–22° C. in winter and summer.

*Rooting habit.*—Spreading, roots do not form tubers.

*Time for shoot development.*—6–7 weeks after sticking of top cutting, 7–8 weeks by leaf cutting.

Growing conditions:

*Temperatures.*—For the first 4–5 weeks, day and night 20° C. then 19° C. until flowering.

*Photoperiodic treatments.*—4 weeks after potting use 2 weeks short days and then long days.

*Growth retardation.*—Cycocel.

Plant description:

*Form.*—Spreading.

*Height.*—28–32 cm.

*Width.*—33–36 cm.

*Branching.*—Good.

*Growth habit.*—Upright growth.

Foliage: Dark green.

*Color.*—Upper side: R.H.S. 147A. Under side: R.H.S. 148 B.

*Veination.*—Palmate; color R.H.S. 148D.

*Shape.*—More or less reniform.

*Size.*—Juvenile leaf: Width 80 mm, length 70 mm. Mature leaf: Width 115 mm, length 100 mm.

*Margin.*—Bi-serrate.

*Tip.*—Attenuated.

*Base.*—Narrow sinus between basal lobes.

*Attachment.*—Stalked, length of petiole 70 mm.

*Texture.*—Quite stiff, leathery, and about 1 mm thick.

Flowering description:

*Flowering habit.*—Floriferous with branched inflorescence.

*Natural flowering season.*—Mid-February through November.

*Flower bud description.*—*Sepals are light green turning a little reddish at the tip.*

*Flowers borne.*—From axillary buds.

Flower: Double flowering.

*Pistil.*—Absent.

*Stamen.*—Absent.

*Quantity.*—7–9 flowers from one stem out of axillary bud.

Petals:

*Color.*—Outer petal, upper side: R.H.S. 44A. Outer petal, under side: R.H.S. 44C. Inner petal, upper side: R.H.S. 44A. Inner petal, inner side: R.H.S. 46C.

*Number.*—About 20 per flower.

*Margin.*—Entire to slightly crenate toward the tip.

*Shape.*—Very broad obovate.

*Length.*—Outer petal: ca. 30 mm. Inner petal: ca. 20 mm.

*Width.*—Outer petal: ca. 40 mm. Inner petal: ca. 25 mm.

Flower longevity: Very good.

Disease resistance: No resistance, but good tolerance against mildew.

General Observations:

Begonia cultivar 'Bellona' grows vigorously and produces good cuttings that root well. 'Bellona' is very floriferous and exhibits excellent keeping quality including maintenance of the bright orange-red flower color. The cultivar typically holds its blooms about 8–12 weeks in summer and about 6–9 weeks in winter. Many known cultivars do not hold their flowers during the winter. 'Bellona' also keeps its flowers and does not fade when planted outdoors.

I claim:

1. A new and distinct begonia plant named 'Bellona', as described and illustrated.

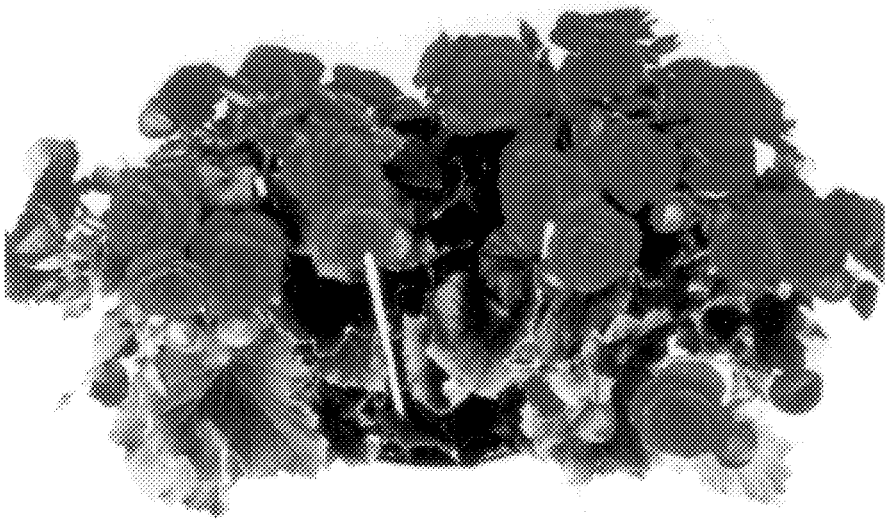

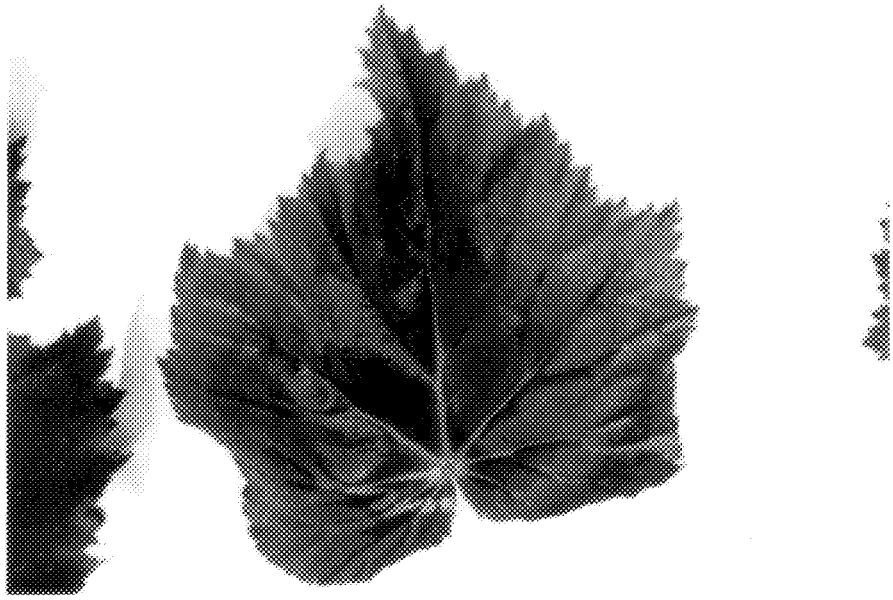

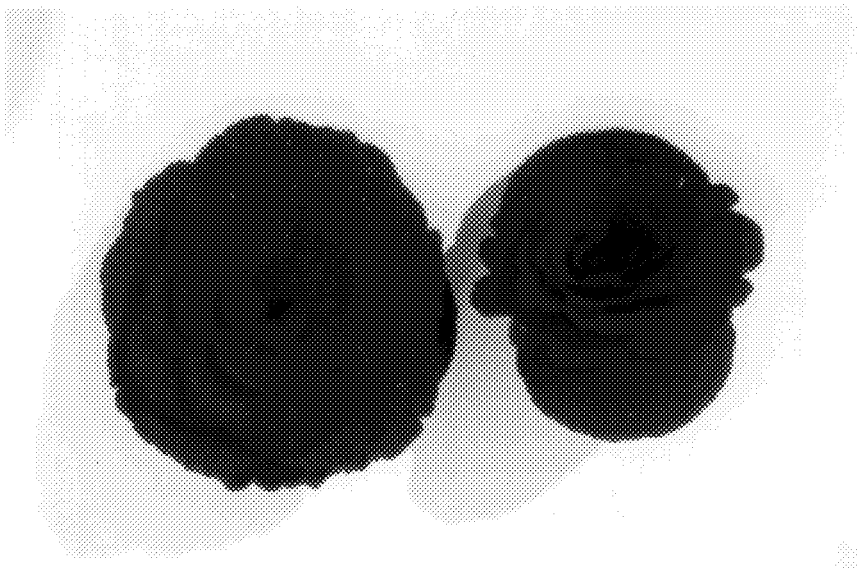

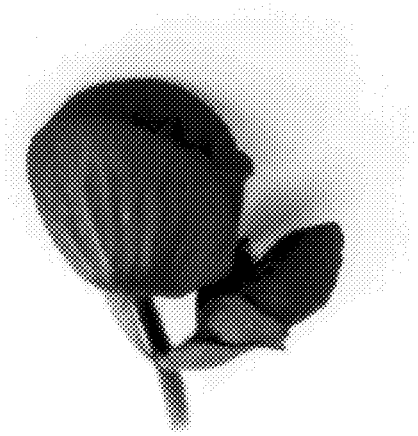

* * * * *